US010786215B2

(12) United States Patent
Nakamura

(10) Patent No.: US 10,786,215 B2
(45) Date of Patent: Sep. 29, 2020

(54) PORTABLE X-RAY IMAGING APPARATUS

(71) Applicant: SHIMADZU CORPORATION, Nakagyo-ku, Kyoto-shi, Kyoto (JP)

(72) Inventor: Toshiaki Nakamura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 61 days.

(21) Appl. No.: 15/981,260

(22) Filed: May 16, 2018

(65) Prior Publication Data

US 2018/0344272 A1    Dec. 6, 2018

(30) Foreign Application Priority Data

May 31, 2017    (JP) ................. 2017-107343

(51) Int. Cl.
| | |
|---|---|
| *A61B 6/08* | (2006.01) |
| *A61B 6/00* | (2006.01) |
| *A61B 6/10* | (2006.01) |
| *A61B 6/06* | (2006.01) |
| *A61B 6/12* | (2006.01) |

(52) U.S. Cl.
CPC ............ *A61B 6/4405* (2013.01); *A61B 6/06* (2013.01); *A61B 6/08* (2013.01); *A61B 6/10* (2013.01); *A61B 6/105* (2013.01); *A61B 6/12* (2013.01); *A61B 6/461* (2013.01); *A61B 6/467* (2013.01); *A61B 6/4452* (2013.01)

(58) Field of Classification Search
CPC .. A61B 6/12; A61B 6/461; A61B 6/06; A61B 6/08; A61B 6/10; A61B 6/105; A61B 6/4452; A61B 6/467
See application file for complete search history.

(56) References Cited

U.S. PATENT DOCUMENTS

| | | | |
|---|---|---|---|
| 9,668,708 B2 | 6/2017 | Okuno et al. | |
| 10,004,469 B2 * | 6/2018 | Neumann | A61B 6/4014 |
| 2010/0114308 A1 * | 5/2010 | Maschke | A61B 6/12 623/2.37 |
| 2015/0272516 A1 * | 10/2015 | Litzenberger | A61B 6/548 378/20 |

FOREIGN PATENT DOCUMENTS

JP    6065248    1/2017

* cited by examiner

*Primary Examiner* — David P Porta
*Assistant Examiner* — Fani P Boosalis
(74) *Attorney, Agent, or Firm* — Andrew F. Young, Esq.; Lackenbach Siegel, LLP

(57) ABSTRACT

A portable X-ray imaging apparatus is prevented from losing a connection with a medical member when a detection element is set up in the proximity of the subject to carry out an X-ray imaging. The portable X-ray imaging apparatus 100 comprises an X-ray tube device 4 that irradiates an X-ray to a subject P, an X-ray receiver 6 that detects the X-ray that transmits the subject P, a housing 1*b* that houses the X-ray receiver 6 capable of being pulled out, and a control element 21 that provides an alarm to prompt paying attention based on the connecting information 30*a* relative to a connection of the medical member with the subject P.

8 Claims, 10 Drawing Sheets

PORTABLE X-RAY IMAGING APPARATUS

CROSS REFERENCE TO RELATED APPLICATIONS

This application relates to, and claims priority from, JP 2017-107343 filed May 31, 2017, the entire contents of which are incorporated herein by reference.

FIGURE SELECTED FOR PUBLICATION

FIG. 5

BACKGROUND OF THE INVENTION

Field of the Invention

The present invention relates to a portable X-ray imaging apparatus.

Description of the Related Art

Conventionally, it is known that a portable (mobile and visiting-room) X-ray imaging apparatus capable of pulling out the X-ray detector and housing therefor (Patent Document 1).

Patent Document

The above Patent Document 1 discloses the portable X-ray imaging apparatus comprising the X-ray detector that detects an X-ray irradiated from an X-ray tube and transmits a subject, and a housing that stores the X-ray detector and from which the detector is pulled out. According to the portable X-ray imaging apparatus disclosed in the above Patent Document 1, when the X-ray imaging is not being performed, the X-ray detector is stored in the housing and when the X-ray image is performed, the X-ray detector is pulled out.

RELATED PRIOR ART DOCUMENTS

Patent Document

Patent Document 1: Japanese Patent 6065248 B1

ASPECTS AND SUMMARY OF THE INVENTION

Objects to be Solved

According to the portable X-ray imaging apparatus disclosed in the Patent Document 1, the X-ray imaging is performed at the position at which the X-ray tube (irradiation element) and the X-ray detector (detection element) are in-place in a proximity of the subject and sandwiching the subject. In case, during performing the X-ray imaging, the subject connects medical members such as a monitoring line and a tube for a medical treatment (medical tube), which monitor the subject and so forth. A nurse and so forth connects such medical members to the subject in advance, so that when a person (e.g., radiology technician) other than the nurse, who connected, carries out the X-ray imaging and such person sets up the X-ray tube and the X-ray detector in a proximity of the subject to carry out the X-ray imaging, it is problematic that each connection between medical members may be lost.

The present invention has been proposed in order to solve the aforementioned problems, and an object of the present invention is to provide a portable X-ray imaging apparatus that prevents the connection of the medical members from losing when the detection element is set up in the proximity of the subject to carry out the X-ray imaging.

Means for Solving the Problem

To achieve the above object, according to one aspect of the present invention, the portable X-ray imaging apparatus comprising: an X-ray irradiation element that irradiates an X-ray to a subject; a detection element that detects the X-ray that transmits through the subject; a housing that houses the detection element capable of being pulled out; a control element that controls the alarm to notify based on the connecting (state) information relative to the connection of the medical member with the subject.

According to another aspect of the present invention, the portable X-ray imaging apparatus comprises the control element that controls the alarm to notify an attention based on the connecting information relative to the connection of the medical member to the subject. Accordingly, when the medical member is connected to the subject, the portable X-ray imaging apparatus prompts the person in charge of the X-ray imaging to pay attention. As a result, the person in charge of the X-ray imaging sets up the X-ray detection element in the proximity of the subject subjected to the X-ray imaging while understanding the connecting state of the medical member to the subject, so that lost-connection (being out of the connection) of the medical member is preventable.

According to another aspect of the present invention, relative to the portable X-ray imaging apparatus, it is preferable that the medical member includes a monitoring line to monitor the physical activity of the subject and a medical tube. Now, it is undesirable that each of the connecting state of the monitoring line and the medical tube is lost, so that the application of the present invention is particularly useful for preventing the medical member from the unconnected state.

According to another aspect of the present invention, it is further preferable that the portable X-ray imaging apparatus comprises an acquisition element capable of acquiring the imaging order information, including the connecting information, of the subject, and the control element provides an alarm based on the connecting information included in the imaging order information acquired by the acquisition element. According to such aspect, it is understandable that the person in charge of the X-ray imaging comprehends (recognizes) the connecting state of the medical member to the subject when checking the X-ray imaging order information of the subject upon carrying out the X-ray imaging. As a result, when the medical member is connected to the subject, the portable X-ray imaging apparatus facilitates to prompt the person in charge of the X-ray imaging to pay attention.

According to another aspect of the present invention, it is further preferable that the portable X-ray imaging apparatus comprises a display element and the control element provides an alarm with displaying the connecting information on the display element. According to such aspect, it is understandable that the person in charge of the X-ray imaging comprehends (recognizes) the connecting state of the medical member to the subject visually and easily.

According to another aspect of the present invention, it is further preferable that the portable X-ray imaging apparatus comprises a lamp that lights to make sure the irradiation field of the irradiation element, and the control element provides an alarm with either of lighting the lamp and blinking the lamp when the connecting information are available.

According to such aspect, it is understandable that the person in charge of the X-ray imaging comprehends (recognizes) the connecting state of the medical member to the subject visually and easily.

In such case, it is preferable that the control element provides an alarm with either of lighting the lamp and blinking the lamp having a different color from that in the case when the irradiation field is adjusted. According to such aspect, the person in charge of the X-ray imaging comprehends (recognizes) the connecting state of the medical member to the subject visually and easily.

According to another aspect of the present invention, it is further preferable that the portable X-ray imaging apparatus comprises a locking element that locks the detection element subjecting to the lock state in which the detection element cannot be pulled out from the housing, and the control element provides an alarm when the connecting information are available and also brings the locking element into the locking state. According to such aspect, when the connecting information are available, the person in charge of the X-ray imaging cannot pull out the detection element from the housing, so that the lost-connection of the medical member can be absolutely prevented when the person in charge of the X-ray imaging sets up the detection element in the proximity of the subject. In addition, both bringing into the locking state in which the detection element cannot be pulled out from the housing and providing the alarm based on the connecting information indicating that the medical member is connected to the subject are carried out, so that the person in charge of the X-ray imaging can more absolutely comprehend that the medical member is connected to the subject.

It is further preferable that the portable X-ray imaging apparatus comprising the above locking element further comprises an operation element is capable of being operative to release the locking state of the locking element. According to such aspect, when the medical member is connected to the subject, the person in charge of the X-ray imaging can release the locking state of the locking element on the basis of checking the connection of the medical member to the subject. As a result, the person in charge of the X-ray imaging sets up the X-ray detection element in the proximity of the subject subjected to the X-ray imaging while absolutely understanding the connecting state of the medical member to the subject.

According to another aspect of the present invention, it is further preferable that the control element provides the alarm when the connecting information, indicating that the medical member is connected to the back-side of the subject, are available. Now, the medical member connecting to the back-side of the subject is particularly hard to be comprehended, so that the application of the present invention is particularly useful for preventing the medical member from the unconnected state.

Effect of the Invention

Accordingly, the present invention provides a portable X-ray imaging apparatus that is prevented from losing the connection of the medical members when the detection element is set up in the proximity of the subject to carry out the X-ray imaging.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
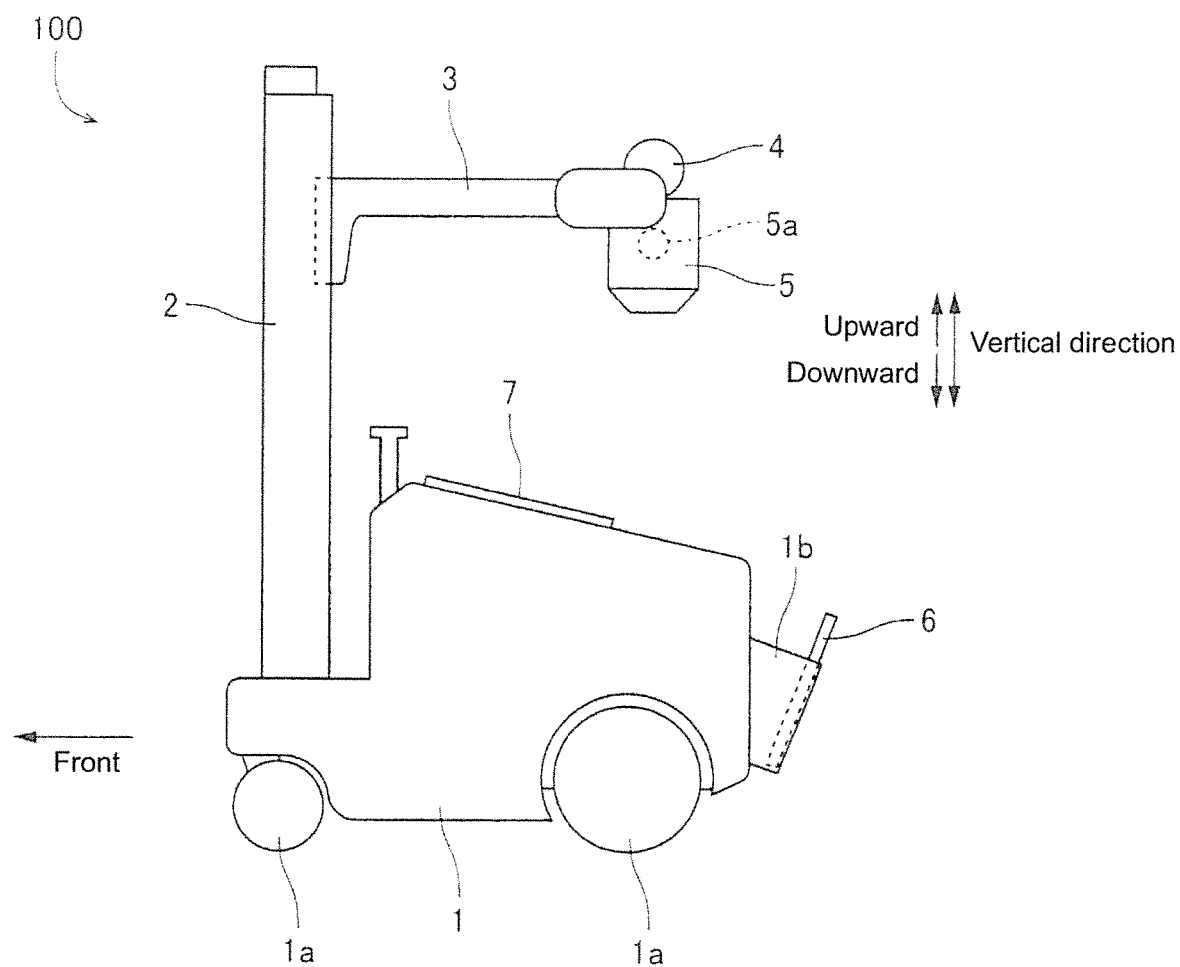
FIG. 1 is a schematic view illustrating an entire structure of a portable X-ray imaging apparatus according to the aspect of the Embodiment 1 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiment 1

Figure 2:
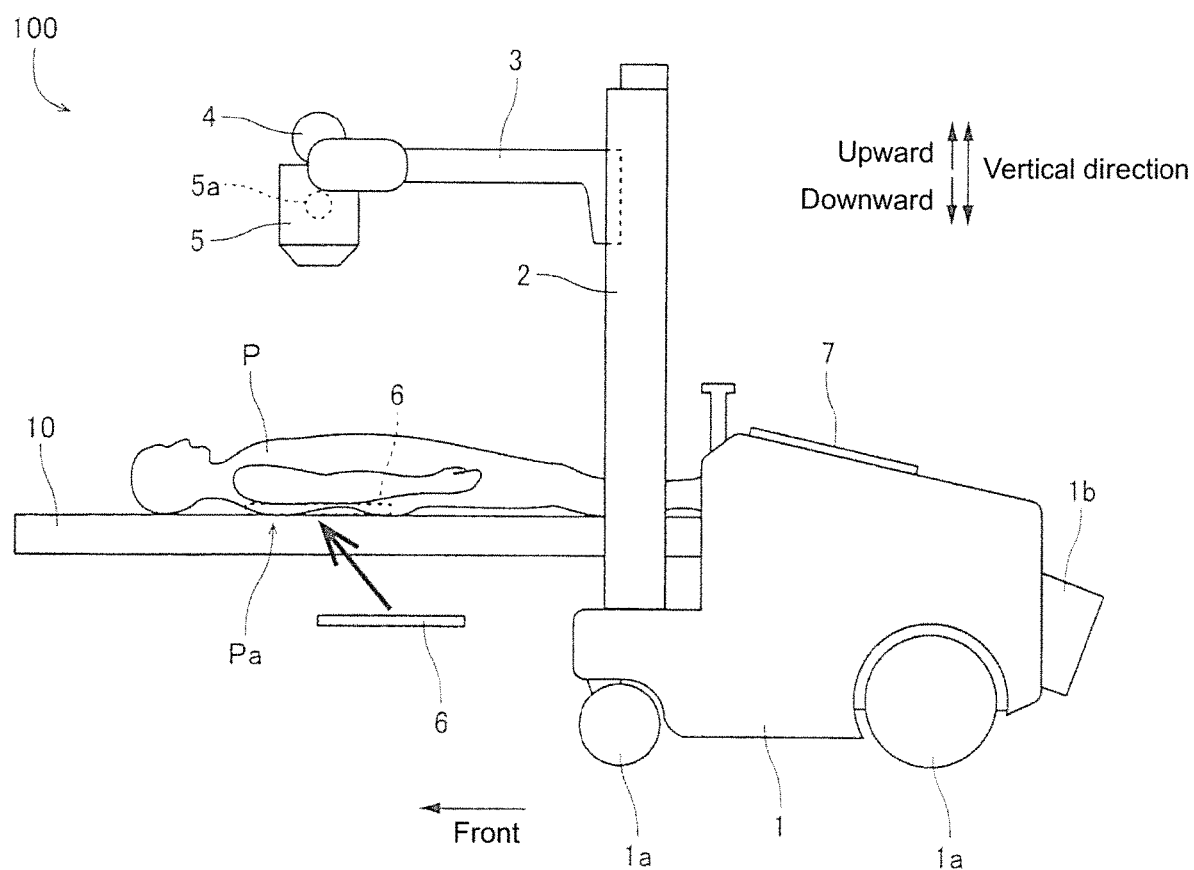
FIG. 2 is a schematic side view illustrating an aspect in which the portable X-ray imaging apparatus is performing an imaging according to the aspect of the Embodiment 1 of the present invention.
Figure 3:
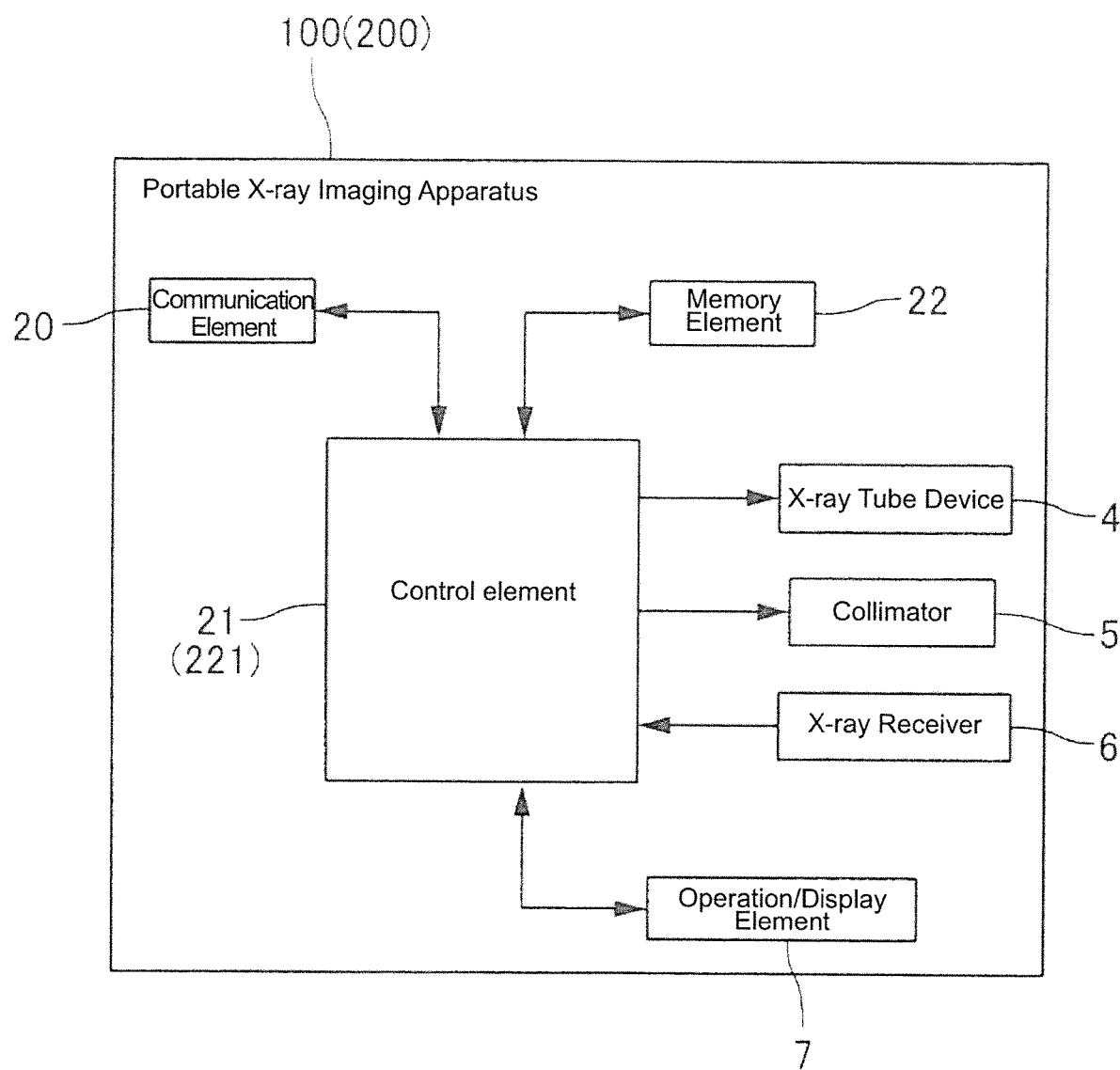
FIG. 3 is a block diagram illustrating a control system of the portable X-ray imaging apparatus according to the aspect of the Embodiment 1 and the Embodiment 2 of the present invention.

Referring to FIG. 1 to FIG. 3, the inventor sets forth the system configuration of the portable X-ray imaging apparatus 100 according to the aspect of the Embodiment 1 of the present invention.

[System of an X-Ray Imaging Apparatus]

Referring to FIG. 1, a portable (mobile) X-ray imaging apparatus 100 according to the aspect of the Embodiment 1 is movable as a whole, and when visiting a patient, the operator can move the apparatus to each patient room where the patient (patient P referring to FIG. 2) is in the hospital to carry out an X-ray imaging. The portable X-ray imaging apparatus 100 comprises a main element 1, a support column 2, an arm 3, an X-ray tube device 4, a collimator 5, an X-ray receiver 6 and a display-operation element 7. Specifically, the X-ray tube 4 is an example of an "X-ray irradiation element" in claim. Further, the X-ray receiver 6 is an example of a "detection element" in claim. Further, the display-operation element 7 is an example of the "display" and the "operation element" in claim.

The main body element 1 is operative as the wheeled platform of the portable X-ray imaging apparatus 100 and includes a power source battery and so forth (are not shown in FIG.) inside thereof. In addition, a plurality of wheels 1a, 1a, are installed to the bottom of the main body element 1, so that the portable X-ray imaging apparatus 100 is movable. In addition, a housing 1b that houses the X-ray receiver 6 capable of being pulled out is installed in the posterior section of the main element 1.

The support column 2 is vertically installed in an anterior section of the main body element 1. The inside of the support column 2 is hollow and the components (eventually the X-ray tube device 4 and the collimator 5) that allow the arm element 3 to lift-lower are housed inside thereof. In addition, the support column 2 is rotatable in the horizontal direction and is operative to move the X-ray tube device 4 to the anterior position of the support column 2 indicated in FIG. 2 from the position where the X-ray tube device 4 indicated in FIG. 1 is in-place in the posterior state of the support column 2.

The arm 3 is installed to be extending from the support column 2 in the horizontal direction. In addition, the arm 3 is liftable and lowerable relative to the support column 2 and in addition, elongates and contracts to enable changing the horizontal position of the X-ray tube device 4.

The X-ray tube device 4 comprises the X-ray source and is capable of irradiating an X-ray when an electric voltage is added by an X-ray tube driving element, not shown in FIG.

The collimator 5 that is installed in the proximity of the X-ray tube device 4 relative to the X-ray irradiation direction of the X-ray tube device 4 enables to adjust the irradiation field of the X-ray irradiated from the X-ray tube device 4. The collimator lamp 5a that has the visual light source and is operative to light on when adjusting the irradiation field of the X-ray is installed to the collimator 5. The X-ray irradiation field is confirmed by using the visual light irradiated from the collimator lap 5a without using the X-ray.

The X-ray image receiver 6 includes an FPD (flat panel detector) and is capable of detecting the X-ray. In addition, the X-ray receiver 6 comprises a wireless X-ray detector and is housed in the housing 1b when the X-ray imaging is not running. Referring to FIG. 2, the X-ray receiver 6 is arranged to be in the opposite side (back-side Pa of the subject P, which is the position indicated by the broken lines) of the X-ray tube device 4 so as to sandwich the subject P loaded on the table 10 by the person (radiation technician) in charge of the X-ray imaging.

The display-operation element 7 comprises e.g., a liquid crystal display operative as a touch panel (touchscreen). And the display-operation element 7 is operative to be a display that displays the image obtained by the X-ray imaging and the imaging order information 30 (referring to FIG. 5) and so forth and to be an operation element through which a variety of operations is input.

According to the aspect of the above configuration, the portable X-ray imaging apparatus 100 is capable of irradiating an X-ray from the X-ray tube device 4 under the state in which the subject P is lying down on the table 10, detecting the X-ray, which transmits the subject P, by the X-ray image receiver 6 and implementing the X-ray imaging relative to the subject P.

In addition, referring to FIG. 3, the portable X-ray imaging apparatus 100 further comprises a communication element 20, a control element 21 and a memory element 22. In addition, the communication element 20 is an example of the "acquisition element" element in claim.

The communication element 20 is operative to communicate with an outside network, acquire the imaging order information 30 (referring to FIG. 5) of the subject P and send the image obtained by the X-ray imaging to the outside. In addition, the imaging order information 30 is input into e.g., the outside server, not shown in FIG., by the nurse in advance and sent to the portable X-ray imaging apparatus 100 from the outside. Then, the radiation technician who is rounding or holding in the hospital accompanying the portable X-ray imaging apparatus 100 carries out the X-ray imaging based on the imaging order information 30.

The control element 21 is a computer comprising a CPU (central processing unit), ROM (read only memory) and RAM (random access memory) and so forth. The control element 21 is operative to display the imaging order information 30 acquired by the communication element 20 and the image obtained by X-ray imaging on the display-operation element 7. In addition, the control element 21 controls a variety of configurations of the portable X-ray imaging apparatus 100 based on the operation input from the display-operation element 7.

The memory element 22 includes e.g., a non-volatile memory. And the memory element 22 stores the program that executes the processing by the control element 21 and stores also the imaging order information 30 acquired by the communication element 20 and the images obtained by X-ray imaging.

According to the aspect of the above configuration, the portable X-ray imaging apparatus 100 is operative to carry out the X-ray imaging of the subject P based on the imaging order information 30 acquired from the outside thereof.

(X-Ray Imaging Based on the Imaging Order Information)

Figure 4:
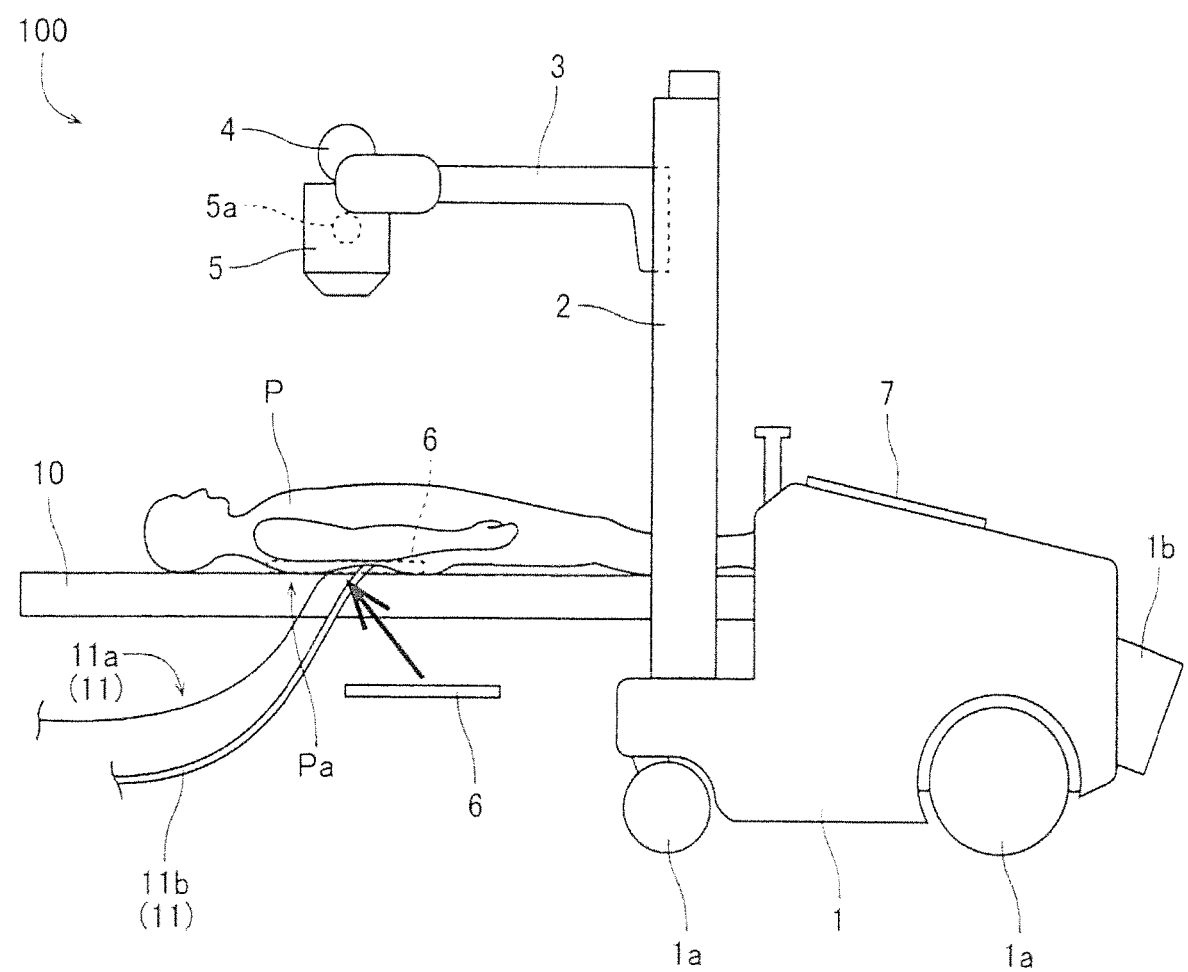
FIG. 4 is an explanatory view illustrating an aspect in which the medical members of the portable X-ray imaging apparatus are connected to the subject according to the aspect of the Embodiment 1 of the present invention.
Figure 5:
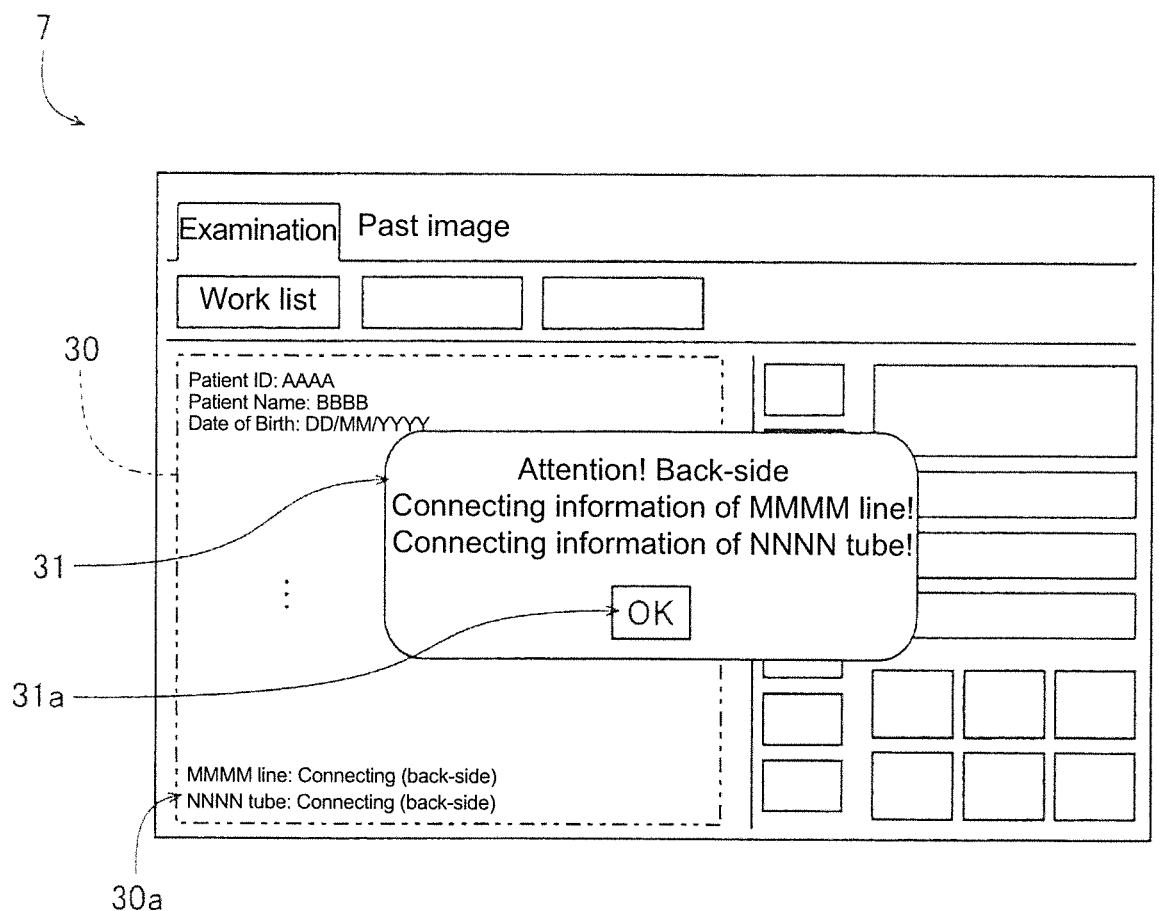
FIG. 5 is an explanatory view illustrating the alarm display when the medical members of the portable X-ray imaging apparatus are connected to the subject according to the aspect of the Embodiment 1 of the present invention.

Next, referring to FIGS. 4 and 5, the inventor sets forth the X-ray imaging based on the imaging order information 30.

Referring to FIG. 5, relative to the portable X-ray imaging apparatus 100, once the communication element 20 acquires the imaging order information 30, the control element 21 controls the display-operation element 7 to display the imaging order information 30. Then the radiation technician carries out the X-ray imaging of the subject P based on such imaging order information 30.

When carrying out the X-ray imaging for the subject P, the X-ray tube device 4 is arranged to be in-place in the suitable position for imaging (in the upper region of the subject P in FIG. 4) and also, the X-ray receiver 6 is pulled out from the housing 1b to be in-place in the opposite-side of the X-ray tube device 4 sandwiching the subject P (the back-side Pa of the subject P in FIG. 4).

Referring to FIG. 4, the subject P subjected to the X-ray imaging may be connected to the medical members 11 by such as a nurse in advance. Now, the medical members 11 are, for example, such as a monitoring line 11a that monitors the physical activities of the subject P and a medical tube 11b and so forth. In such case, the person in charge of the X-ray imaging (radiation technician) must pay attention not to lose erroneously the connecting state of the medical member 11 when arranging the X-ray receiver 6 to the back-side Pa of the subject P. Regardless, referring to FIG. 4, the medical member 11 is located in the position where the medical member 11, which is connected to the back-side Pa of the subject P and is hardly seen due to blocking by the subject P and so forth, so that the radiation technician is in case hard to see the presence of the medical member 11.

Therefore, relative to the portable X-ray imaging apparatus 100 according to the aspect of the available embodiment, the control element 21 controls the alarm to prompt an attention based on the connecting information 30a relative to the connection of the medical member 11 to the back-side Pa of the subject P.

Specifically, referring to FIG. 5, the control element 21 displays the alarm window 31 on the display-operation element 7 when the connecting information 30a of the medical member 11 to the back-side Pa of the subject P is available in the imaging order information 30. The medical member 11 is connected to the back-side Pa of the subject P, so that a message relative to attention that must be paid is displayed on the alarm window 31. In addition, a message confirmation button 31a is displayed in the alarm window 31 and when the radiation technician presses down the confirmation button 31a, the alarm widow 31 disappears. Accordingly, when the medical member 11 is connected to the subject P, the portable X-ray imaging apparatus 100 prompts the radiation technician to pay attention. In addition, referring to FIG. 5, the MMMM line and the NNNNN tube denote the monitoring line 11a and the medical tube 11b respectively.

According to the aspect of the above configuration, the radiation technician understands the connecting state of the medical member 11 to the subject P and consequently, sets up the X-ray receiver 6 in the proximity of the subject P. Accordingly, it is prevented that the radiation technician removes erroneously the connecting state of the medical member 11.

Effect According to the Aspect of the Embodiment 1

The following effects can be obtained according to the aspect of the Embodiment 1.

According to the aspect of the Embodiment 1, as set forth above, the portable X-ray imaging apparatus 100 comprises the control element 21 that controls the alarm to notify based on the connecting information 30a relative to the connection of the medical member 11 with the subject P. Accordingly, when the medical member 11 is connected to the subject P, the portable X-ray imaging apparatus prompts the person in charge of the X-ray imaging to pay attention. As a result, the person in charge of the X-ray imaging sets up the X-ray receiver 6 in the proximity of the subject P subjected to the X-ray imaging while understanding the connecting state of the medical member 11 to the subject P, so that lost-connection (being out of the connection) of the medical member 11 is preventable.

In addition, according to the aspect of the Embodiment 1, the medical members 11 are a monitoring line 11a that monitors the physical activities of the subject P and a medical tube 1ib and so forth. Accordingly, it is prevented that each of the connecting state of the monitoring line 11a and the medical tube 11b, which are not unexpected to be released, is lost.

In addition, according to another aspect of the Embodiment 1, the portable X-ray imaging apparatus 100 comprises a communication element 20 capable of acquiring the image order information 30, including the connecting information 30a, of the subject P, and the control element 21 provides an alarm based on the connecting information 30a included in the imaging order information 30 acquired by the communication element 20. According to such aspect, it is understandable that the person in charge of the X-ray imaging comprehends (recognizes) the connecting state of the medical member 11 to the subject P when checking the X-ray imaging order information 30 of the subject P upon carrying out the X-ray imaging. As a result, when the medical member 11 is connected to the subject P, the portable X-ray imaging apparatus facilitates to prompt the person in charge of the X-ray imaging to pay attention.

According to another aspect of the Embodiment 1, as set forth above, the portable X-ray imaging apparatus 100 comprises the display-operation element 7 and the control element 21 provides the alarm with displaying the connecting information 30a on the display-operation element 7 when the connecting information 30a are available. According to such aspect, it is understandable that the person in charge of the X-ray imaging comprehends (recognizes) the connecting state of the medical member 11 to the subject P visually and easily.

According to another aspect of the Embodiment 1, as set forth above, the control element 21 provides the alarm when the connecting information 30a, indicating that the medical member 11 is connected to the back-side Pa of the subject P, are available. Now, the connecting state of the medical member 11 to the back-side Pa of the subject P is prevented from the unconnected state.

Embodiment 2

Figure 6:
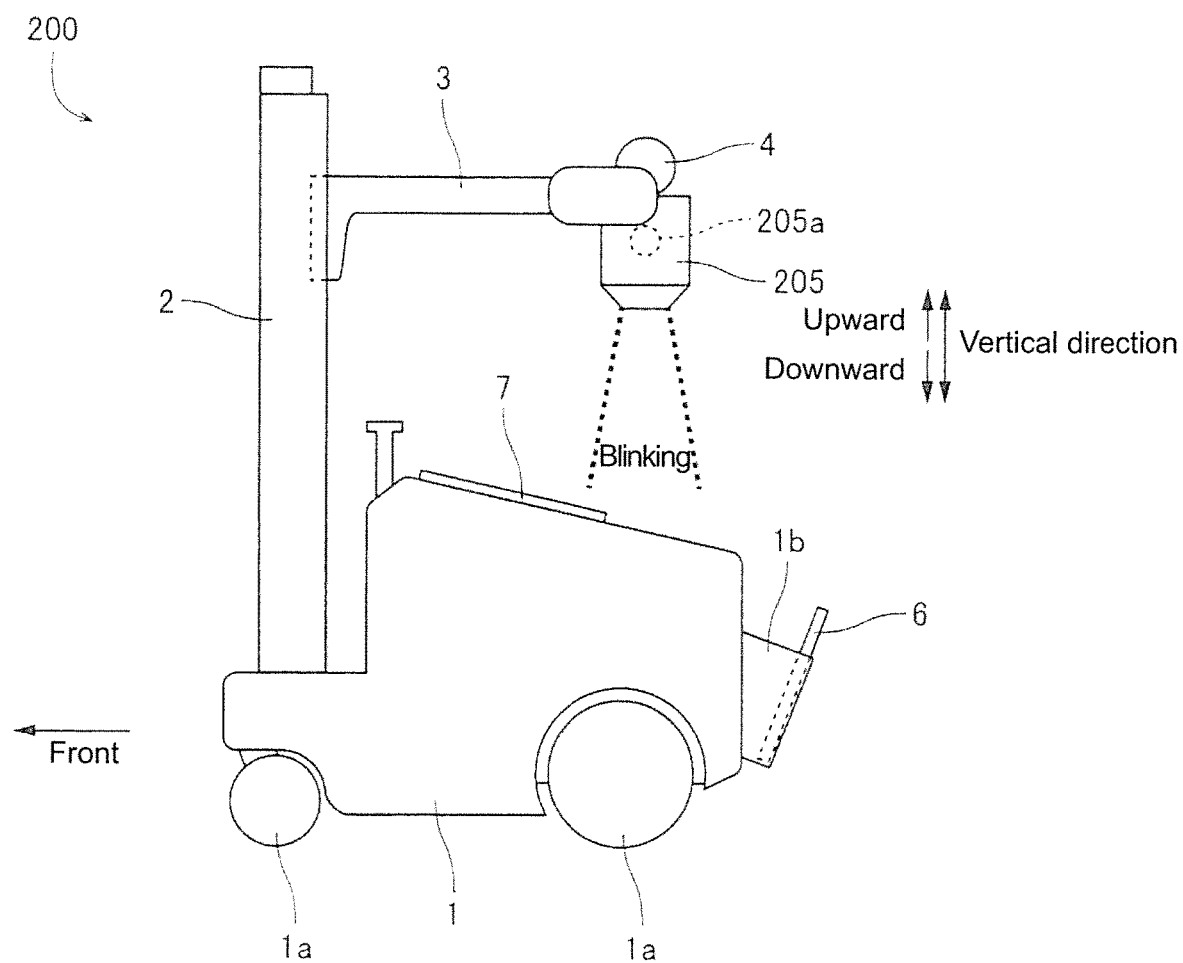
FIG. 6 is an explanatory view illustrating the alarm relative to the portable X-ray imaging apparatus according to the aspect of the Embodiment 2 of the present invention.

Referring to FIG. 3, FIG. 4, FIG. 6, the inventor sets forth the aspect of the Embodiment 2. According to the aspect of the Embodiment 2, the inventor sets forth another Embodiment prompts to pay attention based on the method different from the Embodiment 1 by which the portable X-ray imaging apparatus 100 controls the alarm to notify based on the connecting information 30a relative to the connection of the medical member 11 with the subject P. In addition, the same element as illustrated according to the aspect of the Embodiment 1 has the same sign in FIG.

According to the aspect of the Embodiment 2 of the present invention, the portable X-ray imaging apparatus 200 comprises a collimator 205 having a collimator lamp 205a referring to FIG. 6. The collimator lamp 205a is operative to light on to make sure the X-ray irradiation field of the X-ray tube device 4, as well as the collimator lamp 5a of the portable X-ray imaging apparatus 100 according to the aspect of the Embodiment 1. In addition, the collimator lamp 205a is an example of a "lamp" in claim.

With respect to the portable X-ray imaging apparatus 200, the control element 221 (refer to FIG. 3) blinks the collimator lamp 205a with a different color from the time when the X-ray irradiation field is adjusted, referring to FIG. 6, when the connecting information 30a of the medical member 11 to the back-side Pa (refer to FIG. 4) of the subject P is available in the imaging order information 30. Accordingly, when the medical member 11 is connected to the subject P, the portable X-ray imaging apparatus prompts the radiation technician to pay attention as well as the portable X-ray imaging apparatus 100 according to the aspect of the Embodiment 1. In addition, blinking of the collimator lamp 205a is suspended by the radiation technician with a predetermined operation.

In addition, the configuration of the portable X-ray imaging apparatus 200 according to the aspect of the Embodiment 2 is the same as the aspect of the Embodiment 1.

Effect According to the Aspect of the Embodiment 2

According to the aspect of the Embodiment 2, as set forth above, the portable X-ray imaging apparatus 200 comprises the control element 221 that controls the alarm to notify based on the connecting information 30a relative to the connection of the medical member 11 to the subject P. As a result, the person in charge of the X-ray imaging sets up the X-ray receiver 6 in the proximity of the subject P subjected to the X-ray imaging while understanding the connecting state of the medical member 11 to the subject P, so that lost-connection of the medical member 11 is preventable as well as the portable X-ray imaging apparatus 100 according to the aspect of the Embodiment 1.

According to the aspect of the Embodiment 2, as set forth above, the portable X-ray imaging apparatus 200 further comprises the collimator lamp 205a that lights on to make sure the X-ray irradiation field of the X-ray tube device 4, wherein the control element 21 provides an alarm by blinking the collimator lamp 205a when the connecting information 30a are available. According to such aspect, it is understandable that the person in charge of the X-ray imaging comprehends (recognizes) the connecting state of the medical member 11 to the subject P visually and easily.

In addition, according to another aspect of the Embodiment 2, as set forth above, relative to the portable X-ray imaging apparatus 200, the control element 21 provides the alarm by blinking the collimator lamp 205a with a different color from the color used while adjusting the X-ray irradiation field when the connecting information are available. According to such aspect, it is understandable that the person in charge of the X-ray imaging comprehends (recognizes) the connecting state of the medical member 11 to the subject P visually and easily.

In addition, the other effect according to the aspect of the Embodiment 2 is the same as the aspect of the Embodiment 1.

Embodiment 3

Next, referring to FIG. 7-FIG. 10, the inventor sets forth the aspect of the Embodiment 3. According to the aspect of the Embodiment 3 in addition to the aspect of the Embodiment 1, the inventor sets for a locking state in which the X-ray receiver 6 cannot be pulled out from the housing 1b when the connecting information 30a of the medical member 11 to the subject P are available. In addition, the same element as illustrated according to the aspect of the Embodiment 1 has the same sign in FIG.

Figure 7:
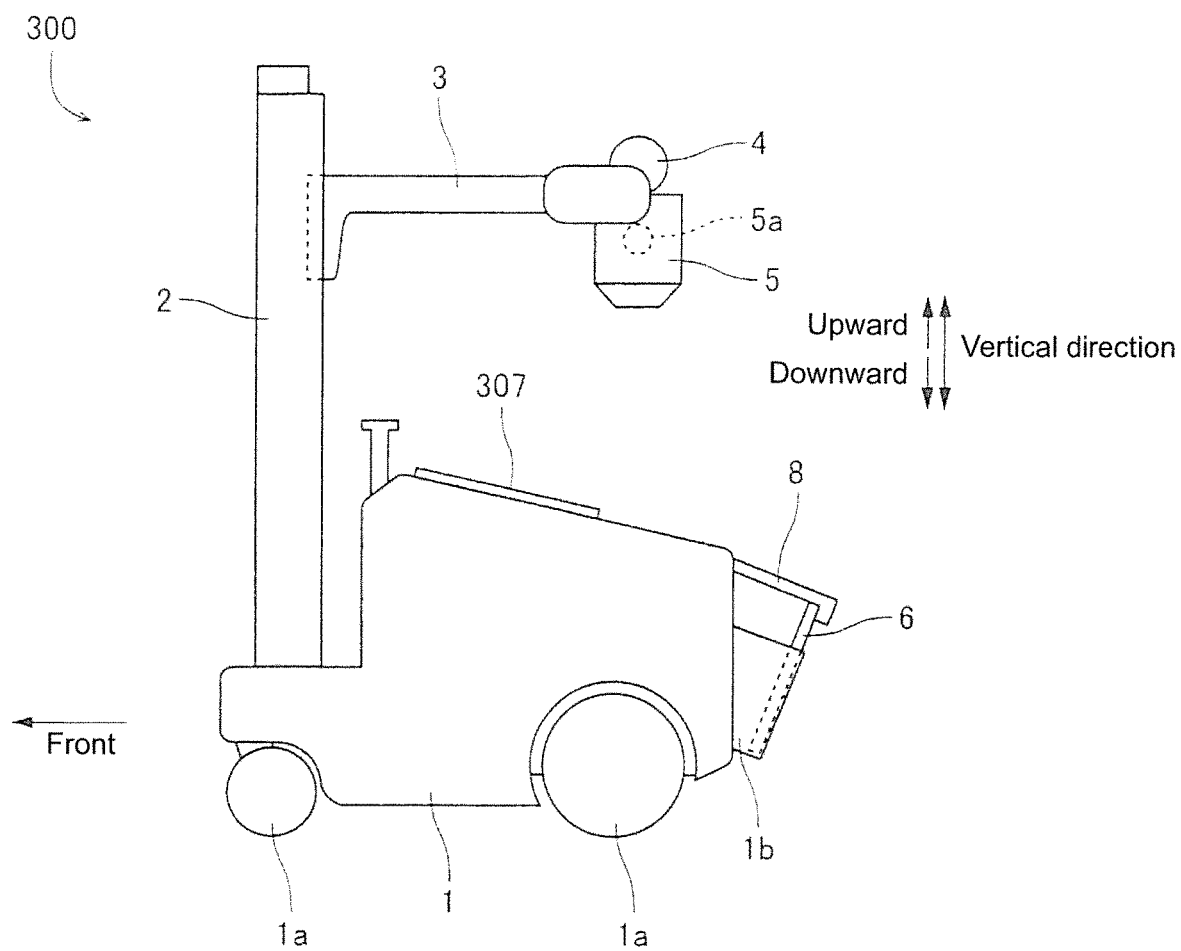
FIG. 7 is a schematic view illustrating an entire structure of a portable X-ray imaging apparatus according to the aspect of the Embodiment 3 of the present invention.

Referring to FIG. 7, according to the aspect of the Embodiment 3 of the present invention, the portable X-ray imaging apparatus 300 comprises a locking element 8 that is formed like a letter L shape and installed in the posterior portion of the main body element 1. The locking element 8 is installed in the upper portion of the housing 1b, and is revolvable between the hooked position to the X-ray receiver 6 (normal position) and the unhooked position to the X-ray receiver 6 (released position referred to FIG. 10) when the X-ray receiver 6 is housed in the housing 1b.

Figure 8:
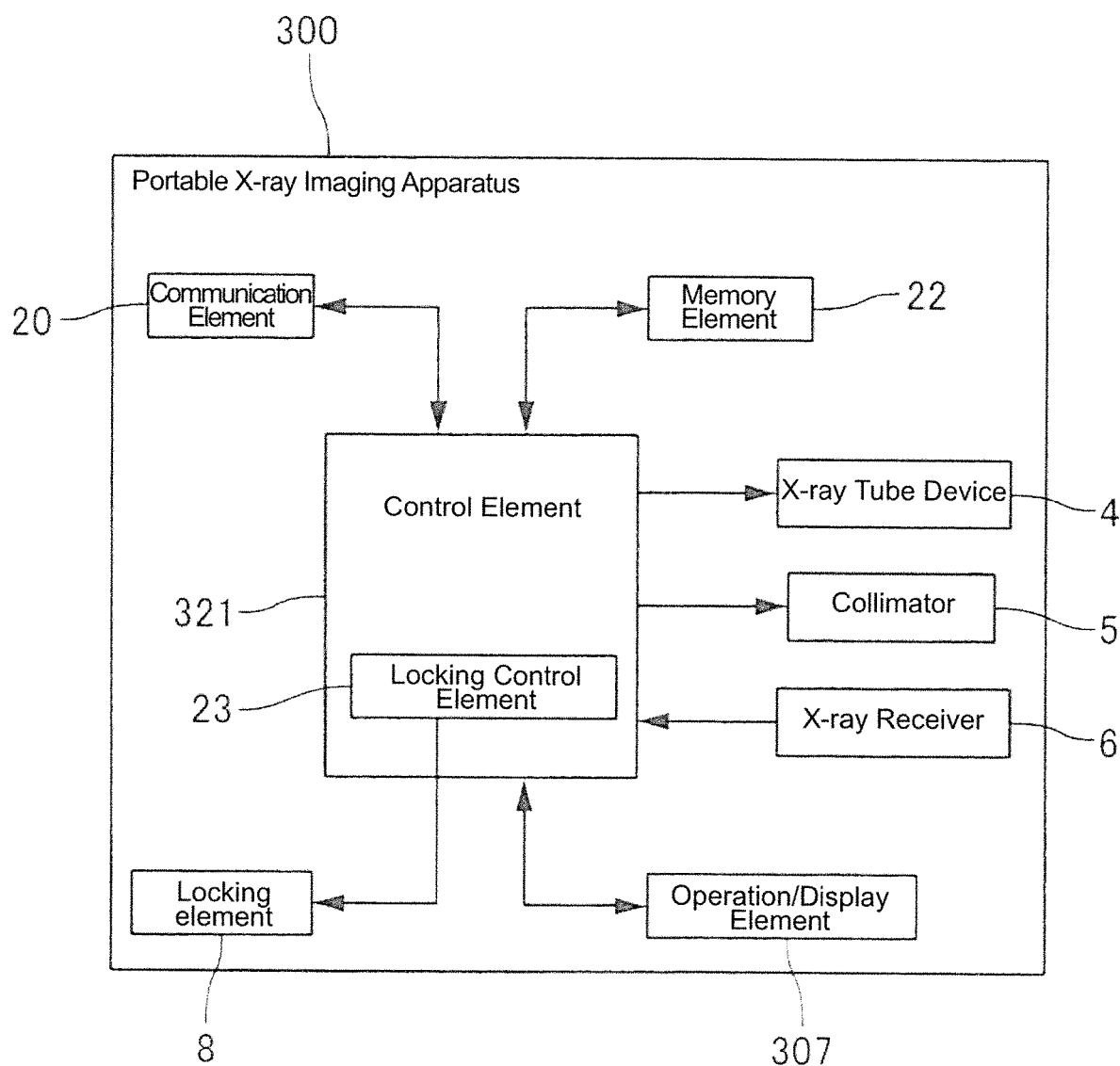
FIG. 8 is a block diagram illustrating a control system of the portable X-ray imaging apparatus according to the aspect of the Embodiment 3 of the present invention.

Referring to FIG. 8, the portable X-ray imaging apparatus 300 comprises a control element 321 having a locking control element 23. The locking control element 23 is operative to control the revolving driving element, not shown in FIG., to lock-and-unlock the locking element 8 at the predetermined position. And the locking control element 23 locks the locking element 8 when the connecting information 30a of the medical member 11 to the back-side Pa of the subject P is available in the imaging order information 30. Accordingly, the locking element 8 controls the radiation technician to pull out the X-ray receiver 6 from the housing 1b.

Figure 9:
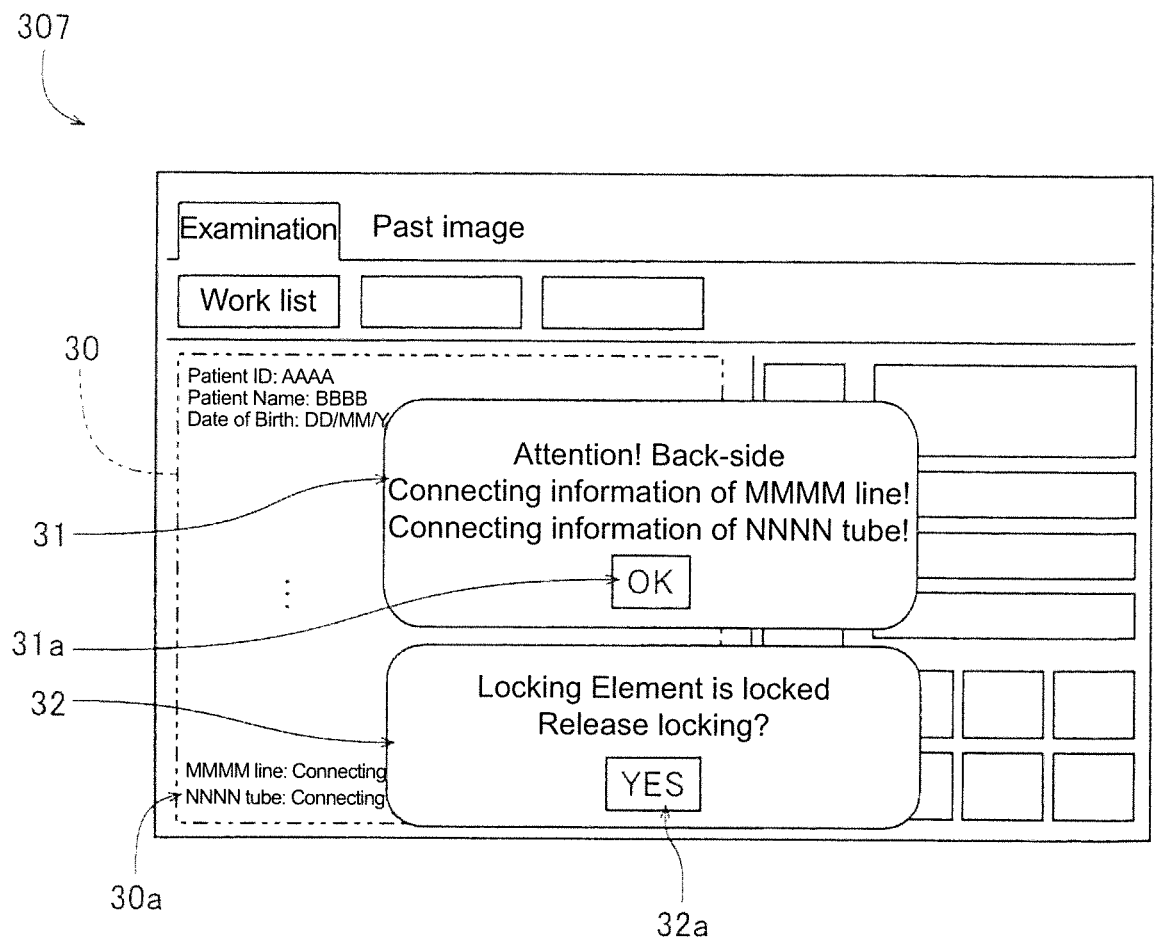
FIG. 9 is an explanatory view illustrating the alarm display when the medical members of the portable X-ray imaging apparatus are connected to the subject according to the aspect of the Embodiment 3 of the present invention.
Figure 10:
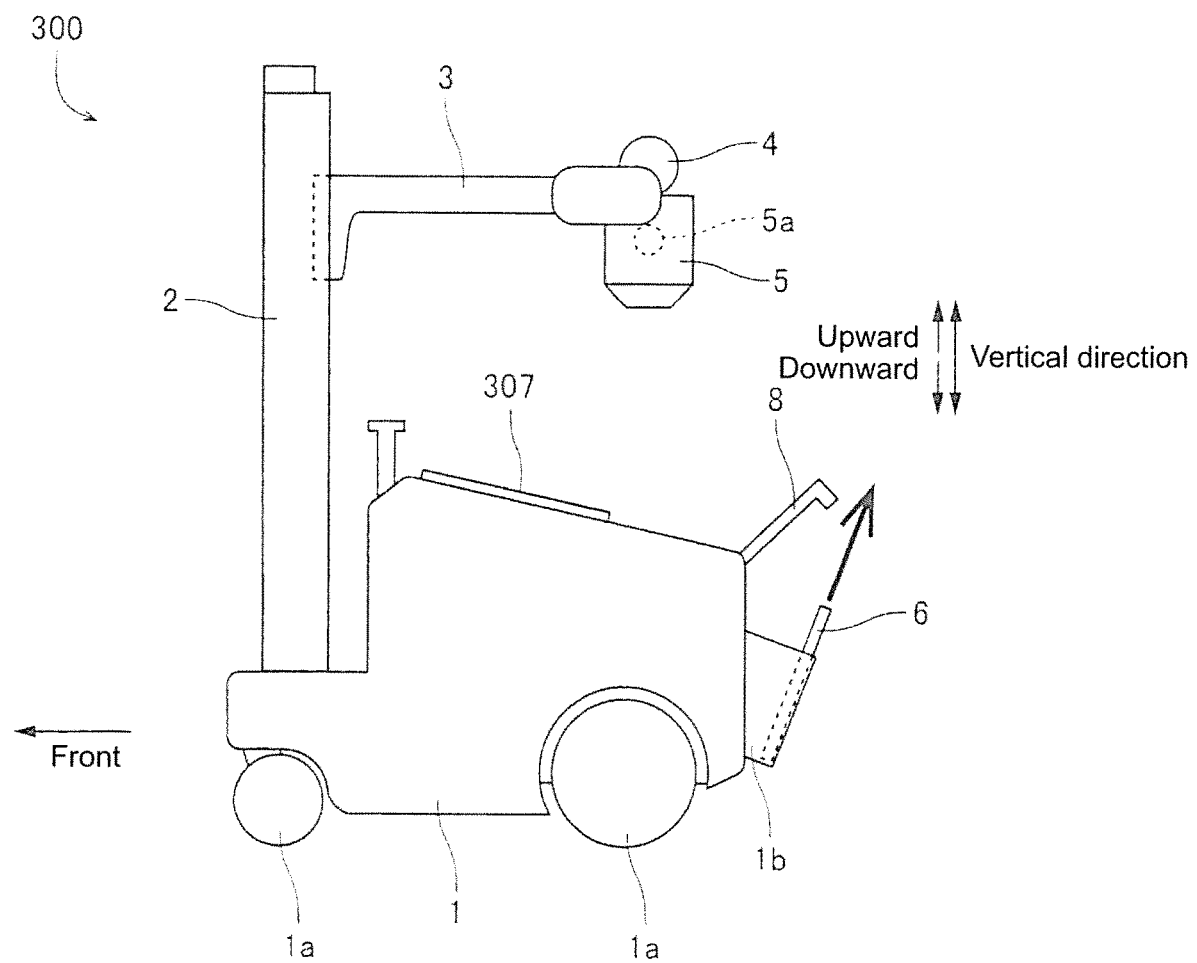
FIG. 10 is a schematic side view illustrating an aspect, in which the locking state of the housing relative to the portable X-ray imaging apparatus is released, according to the aspect of the Embodiment 3 of the present invention.

Referring to FIG. 9, with respect to the portable X-ray imaging apparatus 300, the control element 321 displays the alarm window 31 on the display-operation element 307 when the connecting information 30a of the medical member 11 to the back-side Pa of the subject P is available in the imaging order information 30 as well as the portable X-ray imaging apparatus 100 according to the aspect of the Embodiment 1. In addition, with respect to the portable X-ray imaging apparatus 300, the control element 321 displays the locking information window 32 on the display-operation element 307 in addition to the alarm window 31. The locking information window 32 displays the message indicating that the locking element 8 is locked. According to such aspect, it is understandable that the person in charge of the X-ray imaging absolutely comprehends the connecting of the medical member 11 to the subject P.

The locking information window 32 displays the confirmation button 32a relative to the message. Once the radiation technician presses down the confirmation button 32a, the locking information window 32 disappears and in addition, the locking control element 23 controls the locking element 8 to be out of the locking state. According to such aspect, when the medical member 11 is connected to the subject P, the radiation technician can release the locking state of the locking element 8 following checking the connection of the medical member 11 to the subject P.

In addition, the other configuration according to the aspect of the Embodiment 3 is the same as the aspect of the Embodiment 1.

Effect According to the Aspect of the Embodiment 3

According to the aspect of the Embodiment 3, as set forth above, the portable X-ray imaging apparatus 300 comprises the control element 321 that controls the alarm to notify based on the connecting information 30a relative to the connection of the medical member 11 to the subject P. As a result, the person in charge of the X-ray imaging sets up the X-ray receiver 6 in the proximity of the subject P subjected to the X-ray imaging while understanding the connecting state of the medical member 11 to the subject P, so that lost-connection of the medical member 11 is preventable as well as the portable X-ray imaging apparatus 100 according to the aspect of the Embodiment 1.

In addition, the portable X-ray imaging apparatus 300 further comprises a locking element 8 that locks the X-ray receiver (detection element) 6 into the locking state in which the X-ray receiver 6 cannot be pulled out from the housing 1b, and the control element 321 provides an alarm when the connecting information 30a are available and also brings the locking element 8 into the locking state. According to such aspect, when the connecting information 30a are available, the person in charge of the X-ray imaging cannot pull out the X-ray receiver 6 from the housing 1b, so that the lost-connection of the medical member 11 can be absolutely prevented when the person in charge of the X-ray imaging sets up the receiver 6 in the proximity of the subject P. In addition, both bringing into the locking state in which the X-ray receiver 6 cannot be pulled out from the housing 1b and providing the alarm based on the connecting information 30a indicating that the medical member 11 is connected to the subject P are carried out, so that the person in charge of the X-ray imaging can absolutely comprehend that the medical member 11 is connected to the subject P.

In addition, according to the aspect of the Embodiment 3, as set forth above, the portable X-ray imaging apparatus 300 further comprises the display-operation element 307 that is operative to unlock the locking state of the locking element 8. According to such aspect, when the medical member 11 is connected to the subject P, the person in charge of the X-ray imaging can release the locking state of the locking element 8 following checking the connection of the medical member 11 to the subject P. As a result, the person in charge of the X-ray imaging sets up the X-ray receiver 6 in the proximity of the subject P while absolutely understanding the connecting state of the medical member 11 to the subject P.

In addition, the other effect according to the aspect of the Embodiment 3 is the same as the aspect of the Embodiment 1.

Alternative Embodiment

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the above Embodiments 1-3, an alarm window 31 is respectively displayed on the display-operation element 7 based on the connecting information 30a included in the imaging order information 30 acquired by the communication element 20 or the alarm is provided by blinking the collimator lamp 205a, but the present invention is not limited thereto. According to the aspect of the present invention, a sound can be used to alarm based on the connecting information 30a included in the imaging order information 30 acquired by the communication element 20.

In addition, according to the above Embodiments 1, 2, an alarm window 31 is respectively displayed on the display-operation element 7 based on the connecting information 30a included in the imaging order information 30 acquired by the communication element 20 or the alarm is provided by blinking the collimator lamp 205a, but the present invention is not limited thereto. According to the aspect of the present invention, the alarm window 31 is respectively displayed on the display-operation element 7 based on the connecting information 30a included in the imaging order information 30 acquired by the communication element 20 and the alarm is provided by blinking the collimator lamp 205a together.

In addition, according to the above Embodiments 3, an alarm window 31 is respectively displayed on the display-operation element 7 based on the connecting information 30a included in the imaging order information 30 acquired by the communication element 20 and also the locking element 8 is set up in the locking state in which the X-ray receiver 6 cannot be pulled out from the housing 1b, but the present invention is not limited thereto. According to the aspect of the present invention, the collimator lamp 205a is blinking to provide an alarm based on the connecting information 30a included in the imaging order information 30 acquired by the communication element 20 and the locking element 8 is set up in the locking state in which the X-ray receiver 6 cannot be pulled out from the housing 1b.

In addition, according to the above Embodiments 2, an alarm is provided by blinking the collimator lamp 205a having the different color from the color when adjusting the X-ray irradiation field based on the connecting information 30a included in the imaging order information 30 acquired by the communication element 20, but the present invention is not limited thereto. According to the aspect of the present invention, the alarm can be provided by blinking the collimator lamp 205a having the same color as the color when adjusting the X-ray irradiation field.

In addition, according to the above Embodiments 2, an alarm is provided by blinking the collimator lamp 205a based on the connecting information 30a included in the imaging order information 30 acquired by the communication element 20, but the present invention is not limited thereto. According to the aspect of the present invention, the alarm can be provided by lighting the collimator lamp 205a. In such case, the collimator lamp 205a may light on with the different color from the color when adjusting the X-ray irradiation field or the collimator lamp 205a may light on with the same color from the color when adjusting the X-ray irradiation field.

In addition, according to the above Embodiments 2, an alarm is provided by blinking the collimator lamp 205a based on the connecting information 30a included in the imaging order information 30 acquired by the communication element 20, but the present invention is not limited thereto. According to the aspect of the present invention, when the portable X-ray imaging apparatus comprises a lamp other than the collimator lamp 205a, the alarm can be provided by blinking or lighting such lamp.

In addition, according to the above Embodiments 3, the locking element 8 having the letter-L shape is set up in the locking state at the X-ray receiver 6 is hooked, in which the X-ray receiver 6 cannot be pulled out from the housing 1b based on the connecting information 30a included in the imaging order information 30 acquired by the communication element 20, but the present invention is not limited thereto. According to the aspect of the present invention, any other locking mechanism can be applied as long as the locking state is provided, in which the X-ray receiver 6 cannot be pulled out from the housing 1b.

In addition, according to the aspects of the above Embodiment 1-3, the portable X-ray imaging apparatus 100, 200, 300 having the display-operation element 7 formed of the touch panel liquid crystal display having dual functions of "display" and "operation element" in claim, but the present invention is not limited thereto. According to the present invention, the display and the operation element can be separated. In such case, for example, according to the aspect of the Embodiment 3, the confirmation button 31a and 32b are not displayed relative to the alarm window 31 and the locking information window 32, and the operation element separately installed from the display is pressed down, so that the alarm window 31 and the locking information window 32 disappear.

In addition, according to the above Embodiments 1, 3, an alarm window 31 is displayed on the display-operation element 7 to provide the alarm based on the connecting information 30a included in the imaging order information 30 acquired by the communication element 20, but the present invention is not limited thereto. According to the aspect of the present invention, without displaying the alarm window 31 on the display-operation element 7 based on the connecting information 30a included in the imaging order information 30 acquired by the communication element 20, only the connecting information can be displayed.

According to the aspects of the Embodiment 1-3, as set forth above, the alarm is provided only when the connecting information 30a, indicating that the medical member 11 is connected to the back-side Pa of the subject P, are available, but the present invention is not limited thereto. According to the aspect of the present invention, the alarm can be provided when the connecting information 30a indicating that the medical member 11 is connected to the other position than the back-side Pa of the subject P are available.

According to the aspects of the Embodiment 1-3, as set forth above, the "acquisition element" in claim is the communication element 20 that can acquire the imaging order information 30 from the outside of the portable X-ray imaging apparatuses 100, 200, 300, but the present invention is not limited thereto. According to the aspect of the present invention, the acquisition element can acquire the imaging order information 30 that are directly input to the portable X-ray imaging apparatuses 100, 200, 300 by the radiation technician or the nurse.

REFERENCE OF SIGNS

1b Housing
4 X-ray tube device (Irradiation element)
6 X-ray image receiving element (detection element)
7, 307 Display-operation element (Display, Operation Element)
8 Locking element
11 Medical member
11a Monitoring-line
11b Medical tube
20 Communication element (Acquisition element)
21, 221, 321 Control element
30a Connecting information
100, 200, 300 Portable X-ray imaging apparatus
205a Collimator lamp (Lamp)
P Subject
Pa Back (of Subject)

It will be further understood by those of skill in the art that the apparatus and devices and the elements, modules, circuits, modules and features herein, may without limitation, include any related sub components such as operational structures, a plurality of circuits, resistors, transistors, boards, connectors, communication pathways, and related elements, control elements of all kinds, display circuits and display screens, systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray imaging apparatus, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. As a result is not necessary to list lengthy programming code language as this skill is well within the skill of those in the art. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, interfaces which provides an interface between internal storage device(s) and the other hardware, an peripheral controllers which interface with connected devices such as a backup storage devices, triggers, switches, and circuits, and a network that connects to a hard wired network cable such as Ethernet or may be a wireless connection such as a RF link running under a wireless protocol such as 802.11. A computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module representational images (drawings) executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or information structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce information magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A portable X-ray imaging apparatus comprising:
   an X-ray tube device that irradiates an X-ray to a subject;
   an X-ray receiver that detects the X-ray that transmits through said subject;
   a housing that is operative to house said X-ray receiver in a pullably mobile manner;
   an acquisition unit that acquires imaging order data of said subject;
   a notification unit that notifies a user; and
   a controller;
   wherein said controller further comprises:
      a determining means to determine whether said imaging order data includes connecting information that a medical member is connected to said subject; and
      an instructing means to instruct said notification unit to notify said user when said determining means determines that said imaging order data includes said connecting information.

2. The portable X-ray imaging apparatus, according to claim 1, wherein:
   said medical member is at least one selected from a group consisting of a monitoring line that monitor the physical activity of the subject and a medical tube.

3. The portable X-ray imaging apparatus, according to claim 1, further comprising:
   a display unit; and
   said controller instructs said display unit to notify said user by displaying said connecting information on said display unit by said instructing means when said determining means determines that said imaging order data includes said connecting information.

4. The portable X-ray imaging apparatus, according to claim 1, further comprising:
   a lamp that lights on to confirm an X-ray irradiation field that said tube device provides; and
   said controller instructs said lamp to notify said user by at least one action selected from a group of actions consisting of lighting said lamp and blinking said lamp by said instructing means when said determining means determines that said imaging order data includes said connecting information.

5. The portable X-ray imaging apparatus, according to claim 4, wherein:
   said controller instructs said lamp to notify said user by at least one action selected from said group of actions further consisting of lighting said lamp and blinking said lamp having a different color from a color used when adjusting said X-ray irradiation field by said instructing means when said determining means determine that said imaging order data includes said connecting information.

6. The portable X-ray imaging apparatus, according to claim 1, further comprising:
   a locking unit locks said X-ray receiver that being subjected to a locking state in which said X-ray receiver is incapable of being pulled out from said housing; and
   said controller instructs said notification unit to notify said user by said instructing means and controls said locking unit into said locking state when said determining means determines that said imaging order data includes said connecting information.

7. The portable X-ray imaging apparatus, according to claim 6, further comprising:
   an operation unit that is operative to unlock said locking state of said locking unit.

8. The portable X-ray imaging apparatus, according to claim 1, wherein:
   said controller instructs said notification unit to notify said user by said instructing means when said determining means determines that said imaging order data includes said connecting information that said medical member is connected to a back-side of said subject.

\* \* \* \* \*